United States Patent [19]
Carlson

[11] Patent Number: 5,678,992
[45] Date of Patent: Oct. 21, 1997

[54] NOTCH AND INLET FORMING DENTAL ACCESSORY

[76] Inventor: Carla Carlson, 70 Pocono Rd., Columbus, Ohio 43235

[21] Appl. No.: 574,304

[22] Filed: Dec. 18, 1995

[51] Int. Cl.$^6$ ............................................. A61C 19/00
[52] U.S. Cl. ......................................... 433/34; 433/60
[58] Field of Search ............................... 433/60, 34

[56] References Cited

U.S. PATENT DOCUMENTS

| | | | |
|---|---|---|---|
| 3,965,576 | 6/1976 | Eveland | 433/60 |
| 4,214,367 | 7/1980 | Mack et al. | 433/60 |
| 4,431,409 | 2/1984 | Picard | 433/2 |
| 4,449,931 | 5/1984 | Saito | 433/34 |
| 4,573,917 | 3/1986 | Erickson | 433/60 |
| 4,604,057 | 8/1986 | Viglietti | 433/9 |
| 4,726,768 | 2/1988 | Lee | 433/34 |
| 4,735,569 | 4/1988 | Munk | 433/9 |
| 5,064,368 | 11/1991 | Lavin | 433/2 |
| 5,106,296 | 4/1992 | Varde et al. | 433/60 |

*Primary Examiner*—John J. Wilson

[57] ABSTRACT

A notch and inlet forming dental accessory includes a cylindrical base portion having a first surface and a second surface. The first surface has a circular recess formed therein thereby forming a peripheral wall. The second surface has a circular recess formed therein thereby forming a peripheral wall. A plurality of pegs each have lower ends secured within the circular recess of the first surface of the base portion. A pair of notch projections are secured within the circular recess of the second surface of the base portion.

1 Claim, 3 Drawing Sheets

NOTCH AND INLET FORMING DENTAL ACCESSORY

BACKGROUND OF THE INVENTION

1. Field of the Invention

The present invention relates to a notch and inlet forming dental accessory and more particularly pertains to forming notches and inlets in models for mounting to an articulator with a notch and inlet forming dental accessory.

2. Description of the Prior Art

The use of dental appliances is known in the prior art. More specifically, dental appliances heretofore devised and utilized for the purpose of facilitating accurate dental practices are known to consist basically of familiar, expected and obvious structural configurations, notwithstanding the myriad of designs encompassed by the crowded prior art which have been developed for the fulfillment of countless objectives and requirements.

By way of example, U.S. Pat. No. 5,219,282 to Lavin discloses a dental cast indexing for accurate placement of orthodontic brackets.

U.S. Pat. No. 4,431,409 to Picard discloses an orthodontic apparatus.

U.S. Pat. No. 4,604,057 to Viglietti discloses a cast orthodontic appliance.

U.S. Pat. No. 5,064,368 to Lavin discloses an indexing device for placement of orthodontic brackets.

U.S. Pat. No. 4,735,569 to Munk discloses an orthodontic appliance and method of preparation thereof.

While these devices fulfill their respective, particular objective and requirements, the aforementioned patents do not describe a notch and inlet forming dental accessory for forming notches and inlets in models for mounting to an articulator.

In this respect, the notch and inlet forming dental accessory according to the present invention substantially departs from the conventional concepts and designs of the prior art, and in doing so provides an apparatus primarily developed for the purpose of forming notches and inlets in models for mounting to an articulator.

Therefore, it can be appreciated that there exists a continuing need for new and improved notch and inlet forming dental accessory which can be used for forming notches and inlets in models for mounting to an articulator. In this regard, the present invention substantially fulfills this need.

SUMMARY OF THE INVENTION

In the view of the foregoing disadvantages inherent in the known types of dental appliances now present in the prior art, the present invention provides an improved notch and inlet forming dental accessory. As such, the general purpose of the present invention, which will be described subsequently in greater detail, is to provide a new and improved notch and inlet forming dental accessory and method which has all the advantages of the prior art and none of the disadvantages.

To attain this, the present invention essentially comprises a cylindrical base portion having a first surface and a second surface. The first surface has a circular recess formed therein thereby forming a peripheral wall. The second surface has a circular recess formed therein thereby forming a peripheral wall. A plurality of pegs each have lower ends secured within the circular recess of the first surface of the base portion. Each of the pegs have upper ends extending upwardly above the peripheral wall of the first surface of the base portion. The plurality of pegs are arranged within the circular recess in a circular configuration with a singular peg situated in a center of the circular configuration. A pair of notch projections are secured within the circular recess of the second surface of the base portion. The pair of notch projections each have a height equal to the peripheral wall of the second surface of the base portion.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved notch and inlet forming dental accessory which has all the advantages of the prior art dental appliances and none of the disadvantages.

It is another object of the present invention to provide a new and improved notch and inlet forming dental accessory which may be easily and efficiently manufactured and marketed.

It is a further object of the present invention to provide a new and improved notch and inlet forming dental accessory which is of durable and reliable construction.

An even further object of the present invention is to provide a new and improved notch and inlet forming dental accessory which is susceptible of a low cost of manufacture with regard to both materials and labor, and which accordingly is then susceptible of low prices of sale to the consuming public, thereby making such a notch and inlet forming dental accessory economically available to the buying public.

Still yet another object of the present invention is to provide a new and improved notch and inlet forming dental accessory which provides in the apparatuses and methods of the prior art some of the advantages thereof, while simultaneously overcoming some of the disadvantages normally associated therewith.

Even still another object of the present invention is to provide a new and improved notch and inlet forming dental accessory for forming notches and inlets in models for mounting to an articulator.

Lastly, it is an object of the present invention to provide a new and improved notch and inlet forming dental accessory includes a cylindrical base portion having a first surface and a second surface. The first surface has a circular recess formed therein thereby forming a peripheral wall. The second surface has a circular recess formed therein thereby forming a peripheral wall. A plurality of pegs each have lower ends secured within the circular recess of the first surface of the base portion. A pair of notch projections are secured within the circular recess of the second surface of the base portion.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts through the various Figures.

DESCRIPTION OF THE PREFERRED EMBODIMENT

Figure 1:
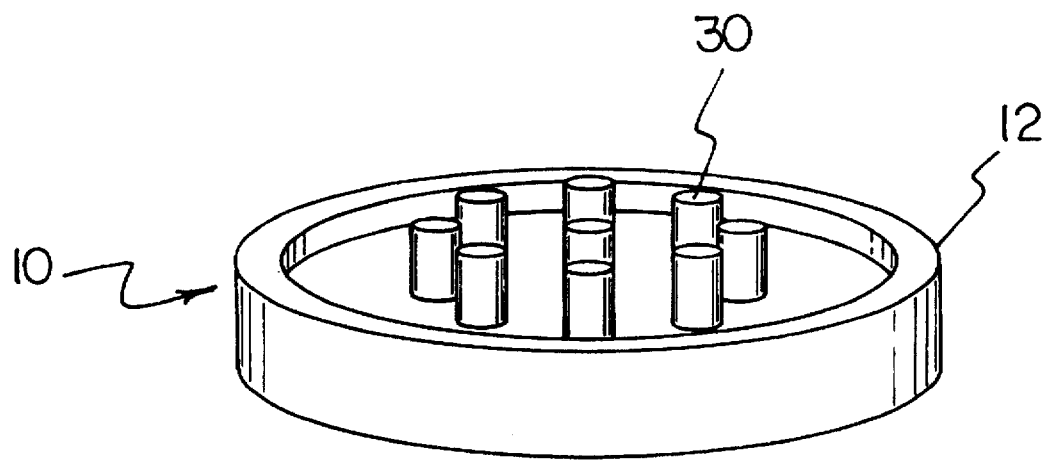
FIG. 1 is a perspective view of the preferred embodiment of the notch and inlet forming dental accessory constructed in accordance with the principles of the present invention.
Figure 2:
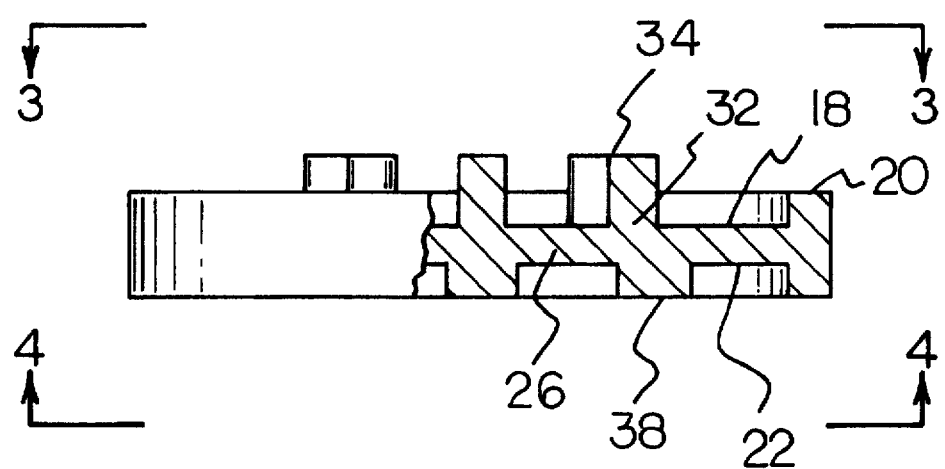
FIG. 2 is a side elevation view of the present invention.
Figure 3:
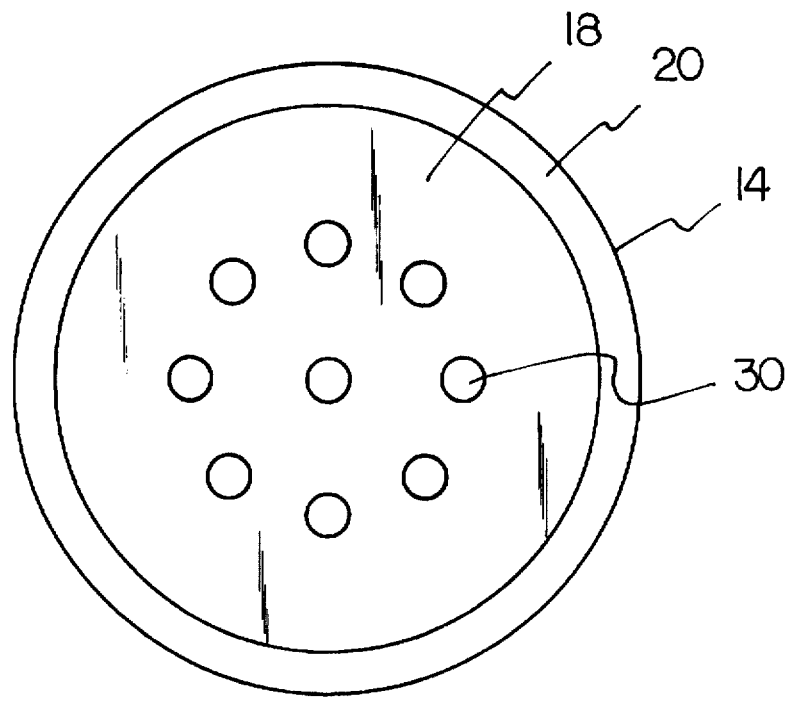
FIG. 3 is a plan view of the present invention taken along line 3—3 of FIG. 2.
Figure 4:
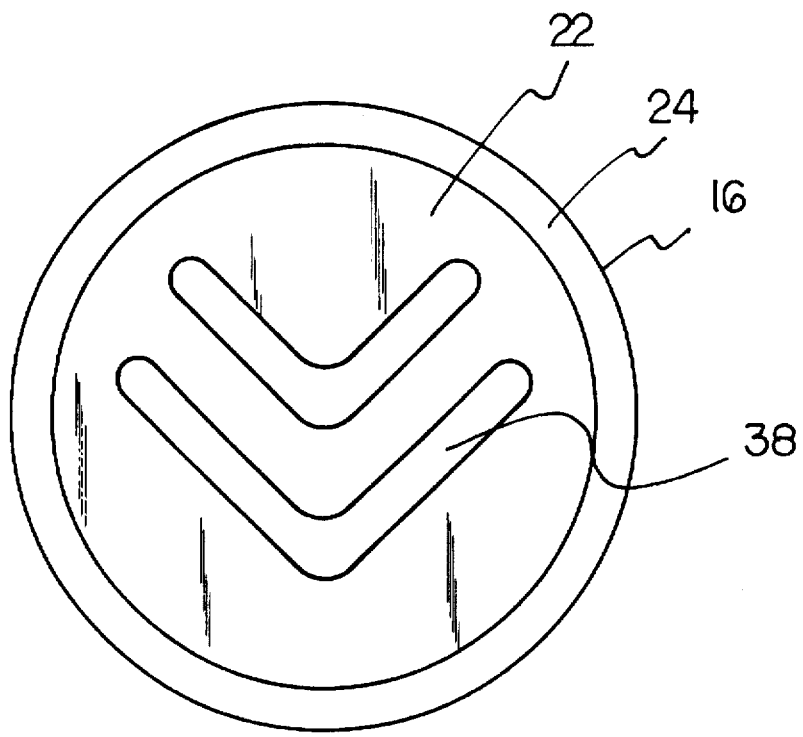
FIG. 4 is a bottom view of the present invention taken along line 4—4 of FIG. 2.
Figure 5:
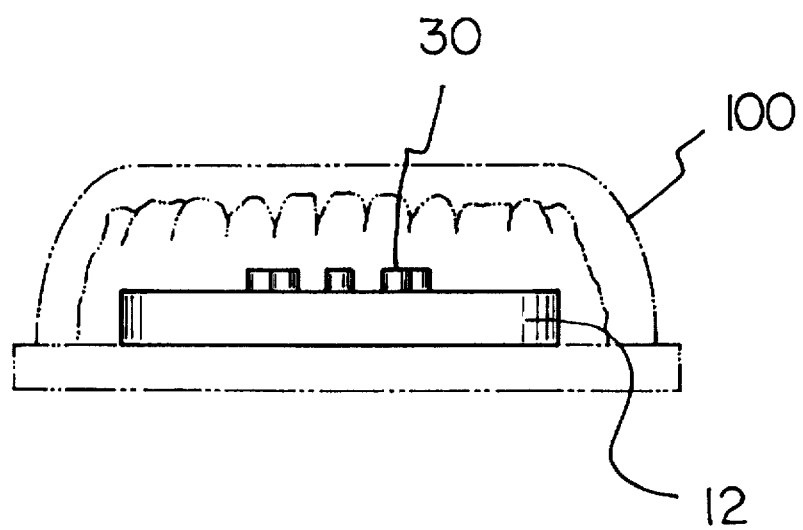
FIG. 5 is a side view of the present invention in place in a cast.
Figure 6:
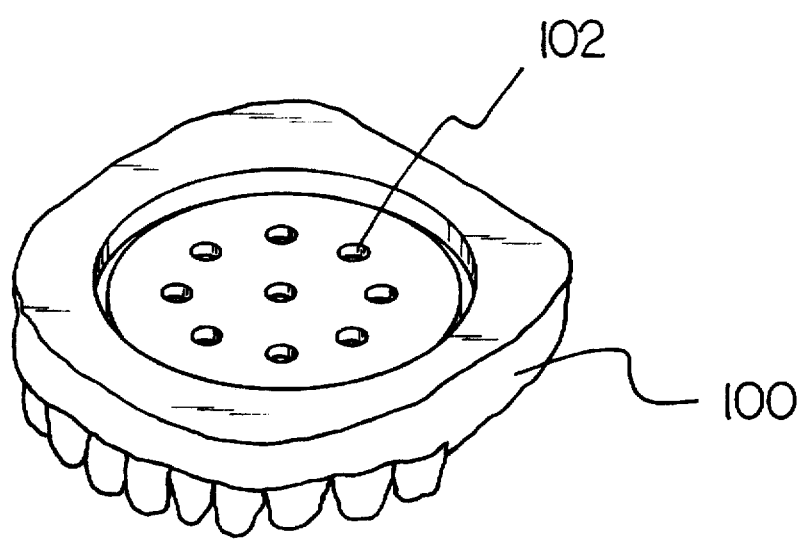
FIG. 6 is a perspective view of a cast after removal of the present invention.

With reference now to the drawings, and in particular, to FIGS. 1-6 thereof, the preferred embodiment of the new and improved notch and inlet forming dental accessory embodying the principles and concepts of the present invention and generally designated by the reference number 10 will be described.

Specifically, it will be noted in the various Figures that the device relates to a new and improved notch and inlet forming dental accessory for forming notches and inlets in models for mounting to an articulator. In its broadest context, the device consists of a cylindrical base portion, a plurality of pegs, and a pair of notch projections. Such components are individually configured and correlated with respect to each other so as to attain the desired objective.

The device 10 includes a cylindrical base portion 12 having a first surface 14 and a second surface 16. The first surface 14 has a circular recess 18 formed therein thereby forming a peripheral wall 20. The second surface 16 has a circular recess 22 formed therein thereby forming a peripheral wall 24. The cylindrical base portion 12 has a base surface 26 separating the first surface 14 from the second surface 16. The cylindrical base portion 12 has a preferred diameter of four inches. The cylindrical base portion 12 has a depth of 1.5 centimeters with the base surface 26 having a thickness of 5 millimeters and each of the peripheral walls 20,24 having a depth of 5 millimeters.

A plurality of pegs 30 each have lower ends 32 secured within the circular recess 18 of the first surface 14 of the base portion 12. Each of the pegs 30 have upper ends 34 extending upwardly above the peripheral wall 20 of the first surface 14 of the base portion 12. Each of the plurality of pegs 30 have a length of about ten millimeters. The plurality of pegs 30 are arranged within the circular recess 18 in a circular configuration with a singular peg situated in a center of the circular configuration. Once wet stone has been poured into an impression 100 of a patient's mouth, the plurality of pegs 30 of the cylindrical base portion 12 are pressed onto the impression. After the stone has set, the base portion 12 is removed with the plurality of pegs 30 having left permanent holes 102 in the impression to allow the impression to be mounted to a mounting plate for studying purposes.

A pair of notch projections 38 are secured within the circular recess 22 of the second surface 16 of the base portion 12. The pair of notch projections 38 each have a height equal to the peripheral wall 24 of the second surface 16 of the base portion 12. Each of the pair of notch projections 38 have a height of about five millimeters. Once wet stone has been poured into an impression of a patient's mouth, the pair of notch projections 38 of the cylindrical base portion 12 are pressed onto the impression. After the stone has set, the base portion 12 is removed with the pair of notch projections 38 having left permanent notches in the impression to allow the impression to be mounted to a mounting plate for studying purposes.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by Letters Patent of the United States is as follows:

1. A notch and inlet forming dental accessory for forming notches and inlets in models for mounting to an articulator comprising, in combination:

a cylindrical base portion having a first surface and a second surface, the first surface having a circular recess formed therein thereby forming a peripheral wall, the second surface having a circular recess formed therein thereby forming a peripheral wall;

a plurality of pegs each having lower ends secured within the circular recess of the first surface of the base portion, each of the pegs having upper ends extending upwardly above the peripheral wall of the first surface of the base portion, the plurality of pegs arranged within the circular recess in a circular configuration with a singular peg situated in a center of the circular configuration, the plurality of pegs providing holes in an impression for mounting to a mounting plate;

a pair of notch projections secured within the circular recess of the second surface of the base portion, the pair of notch projections each having a height equal to the peripheral wall of the second surface of the base portion, the notch projections providing permanent notches in an impression for mounting to a mounting plate.

\* \* \* \* \*